United States Patent [19]

Battistel et al.

[11] Patent Number: 5,302,528
[45] Date of Patent: Apr. 12, 1994

[54] **PROCESS FOR THE ENZYMATIC SEPARATION OF THE OPTICAL ISOMERS OF ALPHA-SUBSTITUTED CARBOXYLIC ACIDS USING ESTERASE FROM *BREVIBACTERIUM IMPERIALE***

[75] Inventors: Ezio Battistel, La Spezia; Daniele Bianchi, Milan; Pietro Cesti, Novara; Giuliana Franzosi, Milan; Roberto Tassinari, Novara; Sandro Spezia, Piacenza, all of Italy

[73] Assignee: Ministero Dell'Universita' E Della Ricerca Scientifica E Tecnologica, Rome, Italy

[21] Appl. No.: 872,108

[22] Filed: Apr. 22, 1992

[30] Foreign Application Priority Data

Apr. 26, 1991 [IT] Italy .................. MI91A001154

[51] Int. Cl.$^5$ ........................... C12P 41/00
[52] U.S. Cl. .................. 435/280; 435/136; 435/840
[58] Field of Search ............ 435/280, 136, 840

[56] References Cited

U.S. PATENT DOCUMENTS

| | | | |
|---|---|---|---|
| 4,857,462 | 8/1989 | Maier | 435/197 |
| 5,037,751 | 8/1991 | Bertola | 435/197 |
| 5,077,217 | 12/1991 | Matson | 435/280 |
| 5,108,917 | 4/1992 | Bertola | 435/280 |

FOREIGN PATENT DOCUMENTS 3919029 12/1990 Fed. Rep. of Germany .......... C12P 41/00

OTHER PUBLICATIONS

Iriuchijima S, Agric Biol Chem 45:1389–92 (81).
Kato Y, Tetra Lett 28:1303–6 (87).
Sugai T, Agric Biol Chem 48:2501–4 (84).
ATCC Catalog pp. 38,64,67,70,131,132 (1989).
"The Prokayotes"; editors Balows et al, pp. I16–17 (1992).

*Primary Examiner*—Douglas W. Robinson
*Assistant Examiner*—S. Saucier
*Attorney, Agent, or Firm*—Oblon, Spivak, McClelland, Maier & Neustadt

[57] ABSTRACT

A process is described for the separation of the optical isomers of alpha-aryl- or alpha-aryloxy- carboxylic acids by means of the stereoselective hydrolysis of racemic alkyl esters of the above acids in the presence of bacteria or their enzymes, selected from the species *Brevibacterium, Bacteridium, Micrococcus,* and *Bacillus.*

6 Claims, 1 Drawing Sheet

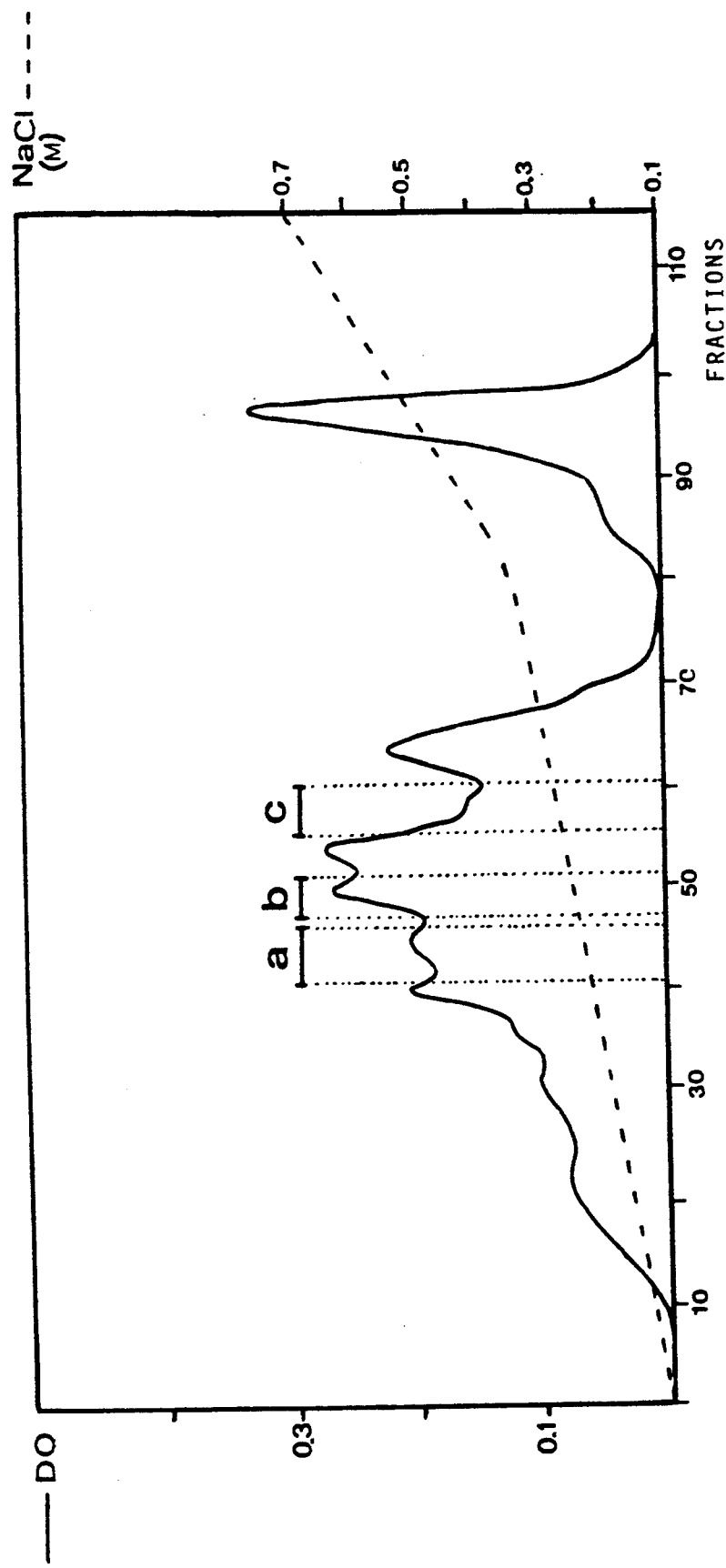

PROCESS FOR THE ENZYMATIC SEPARATION OF THE OPTICAL ISOMERS OF ALPHA-SUBSTITUTED CARBOXYLIC ACIDS USING ESTERASE FROM *BREVIBACTERIUM IMPERIALE*

The present invention relates to a PROCESS FOR THE ENZYMATIC SEPARATION OF THE OPTICAL ISOMERS OF ALPHA-SUBSTITUTED CARBOXYLIC ACIDS HAVING THE GENERAL FORMULA (I):

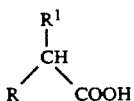

(I)

wherein
R represents a phenyl, naphthyl or phenoxylic group, optionally substituted, with the respective formulae (II), (III) and (IV):

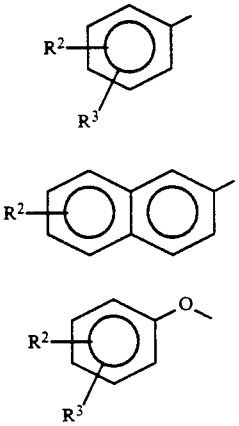

wherein $R^2$ and $R^3$, the same or different, represent a hydrogen atom, a $C_1$–$C_8$ alkyl group, a $C_2$–$C_4$ alkenyl group, a phenyl group, an alkoxylic group, a phenoxylic group, a halogen or a heterocycle product;
$R^1$ represents a $C_1$–$C_4$ alkyl group.

More specifically, the present invention relates to a process which, to obtain the separation of the optical isomers of alpha-substituted carboxylic acids having formula (I) from their racemic mixture, uses a bacterium or an enzyme obtained therefrom, either free or immobilized on suitable supports, which is capable of stereoselectively hydrolyzing the racemic mixture of alkyl esters corresponding to formula (V):

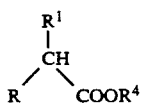

(V)

wherein R and $R^1$ have the above-defined meaning and represents a $C_1$–$C_4$ alkyl group.

The acids corresponding to general formula (I), having an asymmetrical centre in the alpha position, are in fact present in two optically active enantiomorphic forms: S(+) and R(−) and are generally obtained in racemic form.

It is well-known that only one of the two enantiomorphic forms of the above acids or their derivatives have a biological activity and that this activity is considerably higher than that of the other enantiomer present in the racemic mixture.

As a result, for example, only the form R(+) of the derivatives of alpha-phenoxypropionic acids have a weed-killing activity.

In the case of alpha-arylpropionic acids, the form S(+) has a biological activity which is much higher than that of the form R(−), and they are, consequently, generally used in the form S(+) as non-steroid anti-inflammatory drugs: among these are those commercially known as Naproxen, Ibuprofen, Fenopren.

It is therefore evident that there is a wide interest in having an effective method for separating the optically active forms of the acids corresponding to formula (I) to obtain pure enantiomorphic forms.

Procedures for the resolution of the enantiomers of the compounds corresponding to formula (I) are described in the known art (D. G. Kaiser et al., J. Pharm. Science, 2, 269, 1976; A. Frank and C. Ruchards, Chemistry Letters, 1431-34, 1984).

These methods using the classical chemical systems, such as the formation of diastereoisomer salts with chiral amines (ex. methylbenzylamine), have the disadvantages of using costly reagents, of being complicated for the necessary crystallization procedures and, in many cases, of not ensuring satisfactory yields for industrial use.

Methods are also known which use the stereoselective enzymatic hydrolysis of nitriles or amides of the above acids (EP 348.901) or of their particular activated esters as described in EP 159.717. These processes have the disadvantage of starting from substrates which are difficult to prepare and which do not always give products with satisfactory optical purity.

The necessity was consequently felt for having a method of separation which avoided the draw-backs of the known procedures and allowed the resolution of the above acids in a simple and economical way, suitable for industrial use and with a high efficiency.

The Applicant has now found that the separation of the optical isomers of alpha-aryl- or alpha-aryloxy-carboxylic acids can be obtained by means of a biotechnological process of the stereoselective enzymatic hydrolysis of their racemic esters, in the presence of particular bacteria, or the enzymes derived from these, having a stereoselective esterasic activity.

The present invention consequently relates to a process for the enzymatic separation of the optical isomers of alpha-substituted carboxylic acids having the general formula (I):

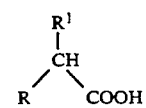

(I)

wherein:
R represents a phenyl group, a naphthyl or phenoxylic group, optionally substituted, corresponding respectively to formulae (II), (III) and (IV):

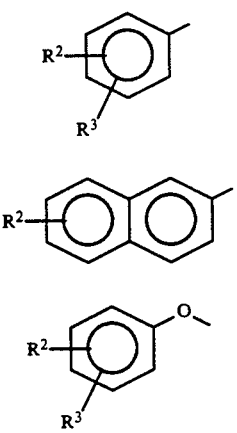

wherein $R^2$ and $R^3$, the same or different, represent a hydrogen atom, a $C_1$-$C_8$ alkyl group, a $C_2$-$C_4$ alkenylic group, a phenyl, alkoxylic, phenoxylic group, a halogen or a heterocycle product;
$R^1$ represents a $C_1$-$C_4$ alkyl group,
which consists of reacting racemic esters having the formula (V):

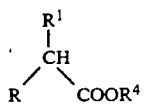

where R and $R^1$ have the meaning previously defined and $R^4$ represents a $C_1$-$C_4$ alkyl group, with a bacterium belonging to the species *Brevibacterium, Bacteridium, Micrococcus, Bacillus* or an esterase enzyme obtained from it, which is capable of selectively hydrolyzing a single enantiomer of the starting racemic ester.

The acid obtained by stereoselective hydrolysis, mainly in the form of a single enantiomer, can be separated from the unreacted ester using the conventional methods.

The racemic esters having formula (V) are already known and can be synthesized using the classical esterification methods of the acids corresponding to formula (I).

Among the bacteria used in the present invention and belonging to the above-mentioned species, the following have proved to be particularly active:

| | |
|---|---|
| *Brevibacterium imperiale* | (CBS 49874) |
| *Brevibacterium spec.* | (CBS 49974) |
| *Bacteridium spec.* | (CBS 49674) |
| *Micrococcus spec.* | (CBS 49774) |
| *Bacillus* | (CBS 49474) |

These bacteria are grown in a standard culture medium using, for example, a sugar as a carbon source, a peptone as a nitrogen source and yeast extracts as a vitamine source.

In the cells of the above bacteria, there are more enzymes having an esterasic activity with differing specifity and stereoselectivity and consequently, by isolating and using the enzyme which has the highest stereoselective activity for that type of bacterium, it is possible to obtain an improvement in the optical purity of the hydrolysis product composed of a single enantiomer corresponding to formula (I).

The hydrolysis process can be carried out using the complete cells of the bacterium or in its culture liquid or its extracts or concentrates; it is also possible to use the particular esterase enzyme in isolated form using the conventional methods such as fractionated precipitation, ion-exchange chromatography or gel-filtration.

The reaction can be carried out by vigorously stirring the suspension composed of the biocatalyst (cells or enzyme) and the racemic ester corresponding to formula (V), in a solution buffered with phosphate ions at pH 7, and at temperatures ranging from 10° C. to 40° C. and preferably from 20° C. to 35° C.

The reagent having formula (V) can be used in a concentration ranging from 0.5% to 10% by weight and preferably from 1% to 5% of the reaction mixture.

The cells are used in a humid weight ratio cells/racemic ester of between 1:10 and 20:1, preferably from 1:2 to 10:1.

Both the bacteria and the enzyme of the present invention can also be used immobilized on suitable substrates of various kinds, selected in accordance with the known art, to increase their stability and facilitate their recovery and re-use.

At the end of the reaction, the acid which has formed, basically in the form of a single enantiomer, and the unreacted ester, are recovered by extraction with a solvent immiscible with water and then separated by subsequent extraction with a 5% aqueous solution of NaOH or by chromatography on silica gel.

The unreacted ester can be racemized again, by treating it with bases in an anhydrous environment, thus enabling it to be recycled in the enzymatic stereoselective hydrolysis process described in the present invention.

The process is particularly advantageous due to its simple and practical conditions.

An interesting aspect is that esters can be used as starting substrates for the stereoselective enzymatic hydrolysis, whose preparation is simple and economical and that single enantiomers of the compounds corresponding to formula (I) are obtained with a high yield and high optical purity.

The following examples provide a better illustration of the present invention but do not limit it in any way.

EXAMPLE 1

Preparation of S(+)2-phenylpropionic acid 500 ml of a sterilized culture medium, containing 1% of yeast extract, 2% of peptone, 1% of glucose and having pH 7, were inoculated with 5 ml of a suspension of *Brevibacterium imperiale* (CBS 49874) in the same medium.

Fermentation was left to continue at 25° C. for 48 hours, stirring at 200 revs per minute.

When the growth had terminated, the cells were recovered by centrifugation (8 g humid weight) and suspended in a phosphate buffer 0.25 N at pH 7 (40 ml).

1 g of (R,S)2-methyl phenylpropionate were added to the suspension and the reaction mixture was stirred at 30° C., the conversion degree being controlled by means of HPLC.

After 48 hours, with a 30% conversion, the reaction was stopped and the pH of the reaction brought to 1 by adding hydrochloric acid and extracting the acid produced and the unreacted ester with ethyl acetate.

The organic phase was then washed with a saturated solution of $K_2CO_3$ at pH 10, thus extracting the acid in the aqueous solution.

The aqueous phase was then re-acidified to pH 2 with HCl and the required acid recovered by extraction with ethyl acetate.

The organic extract was dried and evaporated at reduced pressure and the acid subsequently purified in a chromatographic silica gel column, using hexane/ethyl acetate 8/2 v/v as an eluant.

230 mg of S(+)2-phenylpropionic acid ar obtained with $[a]^{25}_d = +68.2$ (c=1, $CHCl_3$), ee=91%.

The enantiomeric excess (ee) was determined by producing a derivative of the obtained acid by means of S(-)(naphthyl) ethylamine and analysing the diastereoisomeric amide thus obtained by HPLC.

EXAMPLES 2-5

Preparation of S(+)2-phenylpropionic acid

Using the same procedure described in Example 1, the hydrolysis of the methyl (R,S)2-phenylpropionate was carried out using cells of *Brevibacterium spec.* (CBS 49974), *Bacteridium spec.* (CBS 49674), *Micrococcus spec.* (CBS 49774), *Bacillus* (CBS 49474).

The results are shown in Table 1.

TABLE 1

| Microorg. | Time (hrs) | Conv. (%) | (S)2-phenylpropionic acid | |
|---|---|---|---|---|
| | | | $[a]_D$ ($CHCl_3$) | e.e. (%) |
| CBS 49974 | 72 | 30 | +67.4 | 90 |
| CBS 49674 | 76 | 31 | +67.5 | 90 |
| CBS 49774 | 96 | 29 | +69.7 | 93 |
| CBS 49474 | 56 | 32 | +68.2 | 91 |

EXAMPLE 6

Preparation of S(+)2-(4-isobutyl-phenyl)propionic acid (Ibuprofen)

1 g of methyl (R,S)2-(4-isobutyl-phenyl)propionate, in 40 ml of a 0.1M phosphate buffer at pH 7, was added to a suspension of 8 g of *Brevibacterium imperiale* (CBS 49874) cells, obtained in accordance with the procedure described in Example 1. The reaction mixture was stirred at 30° C., and the conversion degree controlled by means of HPLC analysis.

After 72 hours, at a 30% conversion, the reaction was stopped and the required product recovered as indicated in Example 1.

220 mg of S(+)2-(4-isobutylphenyl)propionic acid were obtained with $[a]^{25}_D = +49.5$ (c=1, EtOH), ee=90%.

The enantiomeric excess (ee) was determined, as indicated in Example 1, by means of HPLC.

EXAMPLE 7

Preparation of S(+)2-(6-methoxy-2-naphthyl)propionic acid (Naproxen)

1 g of methyl (R,S)2-(6-methoxy-2-naphthyl)propionate in 40 ml of a 0.1M phosphate buffer at pH 7, was added to a suspension of 10 g of *Brevibacterium imperiale* (CBS 49874) cells, obtained in accordance with the procedure described in Example 1. The reaction mixture was stirred at 30° C., and the conversion degree controlled by means of HPLC analysis.

After 60 hours, at a 30% conversion, the reaction was stopped and the required product was recovered as indicated in Example 1.

210 mg of S(+)2-(6-methoxy-2-naphthyl)propionic acid were obtained with $[a]^{25}_D = +63.5$ (c=1, $CHCl_3$), ee=95%.

The enantiomeric excess (ee) was determined, as indicated in Example 1, by means of HPLC.

EXAMPLE 8

Preparation of R(+)2-phenoxypropionic acid 1 g of methyl (R,S)2-phenoxy-propionate, in 40 ml of a 0.1M phosphate buffer at pH 7, was added to a suspension of 1 g of *Brevibacterium imperiale* (CBS 49874) cells, obtained in accordance with the procedure described in Example 1. The reaction mixture was stirred at 30° C., and the conversion degree controlled by means of HPLC analysis.

After 30 minutes, at a 30% conversion, the reaction was stopped and the required product was recovered as indicated in Example 1.

240 mg of R(+)2-phenoxypropionic acid were obtained with $[a]^{25}_D = +31.7$ (c=1, EtOH), ee=83%.

The enantiomeric excess (ee) was determined by transforming the acid obtained in the corresponding methyl ester and analysing the latter by means of HPLC (Chiralcel Daicel OD chiral column with hexane/isopropanol 9/1 v/v as the eluant).

EXAMPLE 9

Purification of the enzyme having an esterasic activity

The cells (approx. 65 g) taken from 3 litres of culture liquid, were washed with a 0.1M phosphate buffer at pH 7, centrifugated and resuspended in 200 ml of tris 20 mM buffer, NaCl 100 mM at pH 7.5.

A lysis of the cells was then carried out, by means of ultrasonic treatment (250 watts per 5 cycles of 2 minutes at 4° C).

After centrifugation at 20,000 revs per minute, the solution was brought to a 20% saturation with ammonium sulphate at 4° C. and recentrifuged at 20,000 revs per minute for 30 minutes. The surnatant was brought to a 75% saturation by adding a further quantity of ammonium sulphate.

After centrifugation, the heavier portion (5000 mg of proteins) was resuspended in 100 ml of tris 20 mM, NaCl 100 mM buffer at pH 7.5, dialyzed against the same buffer and charged onto a DEAE-Sephacel column (3.2×24 cm) conditioned with the same buffer. The proteins were then eluated with a linear gradient of NaCl from 100 to 400 mM and from 400 to 700 mM.

The esterasic activity was demonstrated by using p-nitrophenylacetate as a substrate.

In FIG. 1, which represents the curve obtained by plotting the number of eluated proteins against the optical density (DO), three areas of major esterasic activity have been found which are indicated as a, b and c. The fractions in area b (90 ml containing 2 mg/ml of proteins) contain the esterasic activity of particular interest.

EXAMPLE 10

Preparation of R(+)2-phenoxypropionic acid 40 ml of fraction b (FIG. 1), obtained as described in Example 5, containing 80 mg of protein are added to 1 g of (R,S)2-phenoxypropionic acid suspended in 30 ml of 0.01 M phospate buffer at pH 7.

Hydrolysis is carried out, under stirring, at a temperature of 30° C., the pH 7 being maintained by means of titration with NaOH 0.5 N.

The course of the reaction is followed in HPLC. After 6 hours the reaction is stopped at a 50% conversion and the required product recovered as indicated in Example 1.

400 mg of R(+)2-phenoxypropionic acid are obtained with $[a]^{25}_D = +37.5$ (c=1, EtOH), ee>95%.

The enantiomeric excess (ee) was determined as indicated in Example 4, by means of HPLC.

EXAMPLE 11

Preparation of R(+)2-(4-chloro-phenoxy)propionic acid

The same procedure was used as described in Example 6, reacting 1 g of methyl (R,S)2-(4-chloro-phenoxy)-propionate, suspended in 30 ml of buffer, with 40 ml of the same fraction b (FIG. 1), obtained as described in Example 5, containing 80 mg of protein.

After 7 hours, the reaction was stopped at a 45% conversion. The required product was recovered as indicated in Example 1.

350 mg of R(+)2-(4-chloro-phenoxy)propionic acid are obtained with $[a]^{25}_D = +38.1$ (c=1, EtOH), ee=95%.

The enantiomeric excess (ee) was determined, as indicated in Example 4, by means of HPLC.

We claim:

1. A process for the enzymatic separation of the optical isomers of an alpha-substituted carboxylic ester of the formula (V)

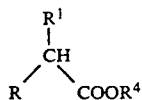
(V)

wherein $R^1$ represents a $C_1$-$C_4$ alkyl group, and wherein R represents a phenyl, naphthyl or phenoxy group, having the formulae (II), (III), and (IV) respectively:

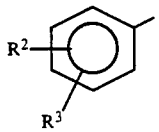
(II)

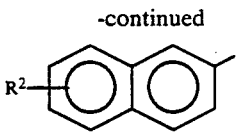
(III)

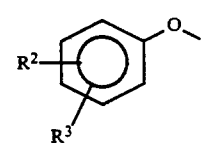
(IV)

wherein $R^2$ and $R^3$ are the same or different and are a hydrogen atom, a $C_1$-$C_8$ alkyl group, a $C_2$-$C_4$ alkenyl group, a phenyl alkoxyl, phenoxyl group, or a halogen, and $R_4$ represents a $C_1$-$C_4$ alkyl group;

comprising the steps of:
(i) reacting said compounds of formula (V) with *Brevibacterium imperiale* (CBS 49874), an esterase obtained therefrom, and
(ii) separating a substantially pure single enantiomer of an acid corresponding to the formula (I),

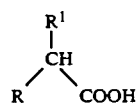
(I)

wherein R and $R^1$ are as defined above.

2. The process in accordance with claim 1, wherein the bacterium or esterase obtained therefrom, is immobilized on suitable carriers.

3. The process, in accordance with claim 1, wherein the selective hydrolysis reaction is carried out in a solution buffered with phosphate ions at a pH of between 6 and 8 and at temperatures ranging from 10° C. to 40° C.

4. The process, in accordance with claim 1, wherein the racemic ester corresponding to formula (V) is present in a concentration of between 0.5% and 10% by weight of the reaction mixture.

5. The process, in accordance with claim 1, wherein the esterase is contained in the cells of the bacterium or in a culture liquid thereof or its extracts or its concentrates.

6. The process, in accordance with claim 1, wherein the cells of the bacterium are present in a wet weight ratio of cells/racemic ester of between 1:10 and 20:1.

* * * * *